US012029534B2

(12) United States Patent
Dey

(10) Patent No.: US 12,029,534 B2
(45) Date of Patent: Jul. 9, 2024

(54) INTELLIGENT CARDIO PULMONARY SCREENING DEVICE FOR TELEMEDICINE APPLICATIONS

(71) Applicant: IBRUM TECHNOLOGIES, Bengaluru (IN)

(72) Inventor: Nibedit Dey, Bengaluru (IN)

( * ) Notice: Subject to any disclaimer, the term of this patent is extended or adjusted under 35 U.S.C. 154(b) by 539 days.

(21) Appl. No.: 17/277,721

(22) PCT Filed: Oct. 8, 2019

(86) PCT No.: PCT/IN2019/050747
§ 371 (c)(1),
(2) Date: Mar. 18, 2021

(87) PCT Pub. No.: WO2020/075190
PCT Pub. Date: Apr. 16, 2020

(65) Prior Publication Data
US 2021/0345890 A1    Nov. 11, 2021

(30) Foreign Application Priority Data

Oct. 10, 2018  (IN) .............................. 201841038460

(51) Int. Cl.
*A61B 5/024*   (2006.01)
*A61B 5/00*    (2006.01)
(Continued)

(52) U.S. Cl.
CPC ............ *A61B 5/024* (2013.01); *A61B 5/0008* (2013.01); *A61B 5/0022* (2013.01); *A61B 5/01* (2013.01);
(Continued)

(58) Field of Classification Search
CPC ........... A61B 5/024; A61B 5/08; A61B 7/003; A61B 2562/0271; A61B 7/02; A61B 7/026; A61B 7/04
See application file for complete search history.

(56) References Cited

U.S. PATENT DOCUMENTS 5,825,895 A  * 10/1998  Grasfield ................. A61B 7/04
                                                     600/528
6,676,600 B1   1/2004   Conero et al.
(Continued)

FOREIGN PATENT DOCUMENTS

| CN | 105962949 A    | 9/2016  |
|----|----------------|---------|
| WO | 2001096986 A2  | 12/2001 |
| WO | 2016110804 A1  | 7/2016  |

OTHER PUBLICATIONS

International Search Report and Written Opinion mailed Jun. 1, 2020 for PCT/IN2019/050747.

*Primary Examiner* — Paula J Stice
(74) *Attorney, Agent, or Firm* — Nasr Patent Law LLC; Faisal K. Abou-Nasr

(57) ABSTRACT

An intelligent and real-time cardio-pulmonary screening device (100) is disclosed. The device comprises a housing that encloses a body, said body comprising: a display unit (101); a plurality of light emitting diode (LED) indicators (102, 103); a first toggle switch (104); a second toggle switch (105); a plurality of volume controls (106, 107); a third toggle switch; an output port (109); a switch (110); a charging port (111); a temperature sensor; a transducer unit (112); and an artificial intelligence module. The artificial intelligence module analyses the sounds received in real-time and presents the results in the display unit (101), as well as in the plurality of the LED indicators (102, 103); it comprises an artificial intelligence processor that is configured to run machine learning algorithms on the device (100), (Continued)

with said artificial intelligence module syncing from and to the cloud when connected to internet. The disclosed device (100) is an easy to use, affordable, point of care screening device that classifies underlying cardio-pulmonary diseases within a minute.

3 Claims, 6 Drawing Sheets

(51) Int. Cl.
  *A61B 5/01* (2006.01)
  *A61B 5/08* (2006.01)
  *A61B 5/145* (2006.01)
  *A61B 7/00* (2006.01)

(52) U.S. Cl.
  CPC ............ *A61B 5/08* (2013.01); *A61B 5/14542* (2013.01); *A61B 5/6823* (2013.01); *A61B 5/725* (2013.01); *A61B 5/7264* (2013.01); *A61B 5/7435* (2013.01); *A61B 5/746* (2013.01); *A61B 5/7465* (2013.01); *A61B 5/7475* (2013.01); *A61B 7/003* (2013.01); *A61B 2503/04* (2013.01); *A61B 2560/0214* (2013.01); *A61B 2562/0271* (2013.01)

(56) References Cited

U.S. PATENT DOCUMENTS

| | | |
|---|---|---|
| 2013/0172691 A1 | 7/2013 | Tran |
| 2015/0099941 A1 | 4/2015 | Tran |
| 2018/0160907 A1* | 6/2018 | Verma ................ A61B 1/00016 |

\* cited by examiner

INTELLIGENT CARDIO PULMONARY SCREENING DEVICE FOR TELEMEDICINE APPLICATIONS

FIELD OF THE INVENTION

The present disclosure is generally related to a device for the screening of cardio-pulmonary conditions. Particularly, it is related to an intelligent cardio-pulmonary screening device, said monitoring occurring in a real-time basis.

BACKGROUND OF THE INVENTION

Infections of the lower respiratory tract are among the leading causes of childhood death worldwide. To diagnose such infections, doctors use the traditional stethoscope to listen to the chest sounds of a patient and recommend subsequent treatment. However, such a method of diagnosis is challenging due to noisy atmosphere and lack of familiarity with all types of sounds. Further, due to lack of specialists in primary care centres and lack of time per patient, patients sometimes remain undiagnosed, which leads to the disease becoming chronic.

The pulmonary examination consists of inspection, palpation, percussion, and auscultation. The inspection process initiates and continues throughout the patient encounter. Palpation, confirmed by percussion, assesses for tenderness and degree of chest expansion. Auscultation, a more sensitive process, confirms earlier findings and may help to identify specific pathologic processes not previously recognized.

The problem is worse for babies suffering from pneumonia, where any delayed diagnosis can be fatal. In a crowded and noisy atmosphere, it is extremely difficult to hear a baby's congested lungs through a normal stethoscope. As per research, physical observation and auscultation are not effective ways to diagnose a baby suffering from pneumonia. Similarly, finding a cardiac abnormality or foetal heart sound is a challenging task.

With the recent development of technologies, a new category of stethoscopes called smart stethoscope has entered the market. Unlike traditional acoustic or electronic stethoscopes, the smart stethoscopes have microphones inside a transducer unit that collects the chest sounds. However, they do not have facilities to analyse the current condition of a patient and provide an immediate result. They only amplify sounds and provide an interface to visualize the waveform on a computer or a mobile phone.

The problem with the smart stethoscope is that doctors are used to working with traditional stethoscope sounds. So, amplification holds little value for them. Apart from this, the user needs to have technical knowledge to interpret the plots. Therefore, the smart or electronic stethoscopes are not suitable for an average healthcare user like paramedical staff. Further, there is no pulmonary specific device which uses lung sounds for automatic analysis of a patient's condition.

There is, therefore, a need in the art for a device that monitors cardio-pulmonary activity in real-time, which overcomes the aforementioned drawbacks and shortcomings.

SUMMARY OF THE INVENTION

An intelligent and real-time cardio-pulmonary screening device is disclosed. The device comprises a housing that encloses a body.

The body comprises: a display unit; a plurality of light emitting diode (LED) indicators; a first toggle switch; a second toggle switch; a plurality of volume controls; a third toggle switch; an output port; a switch; a charging port; a temperature sensor; and a transducer unit.

The plurality of light emitting diode (LED) indicators visually indicates the results of cardio-pulmonary analysis.

The first toggle switch is configured to enable the toggling of the device between a heart monitoring mode and a lung monitoring mode, while the second toggle switch is configured to enable the toggling of the device between an adult mode and a paediatric mode. The third toggle switch is configured to enable the connecting or disconnecting of the device with an application on a handheld device or a wearable device or an application that is installable on a computing device.

The plurality of volume controls facilitate the increasing or decreasing of the volume of an audio output from the device.

The output port facilitates the connecting of an audio playback device; the switch powers the device on or off; the charging port facilities the charging of a rechargeable battery; the temperature sensor facilitates the measuring of the body temperature of a patient; and the transducer unit is configured to enable the device to receive sound from the chest or the lungs of the patient, said transducer unit being removably attached with the device.

An artificial intelligence module analyses the sounds received in real-time and presents the results in the display unit, as well as in the plurality of the LED indicators, said artificial intelligence module comprising an artificial intelligence processor that is configured to run machine learning algorithms on the device, with said artificial intelligence module syncing from and to the cloud when connected to internet; it comprises an artificial intelligence processor that is configured to run machine learning algorithms on the device.

The disclosed device is an easy to use, affordable, point of care screening device that classifies underlying cardio-pulmonary diseases within a minute.

DETAILED DESCRIPTION OF THE INVENTION

Throughout this specification, the use of the word "comprise" and "include" and variations such as "comprises "comprising", "includes", and "including" implies the inclusion of an element or elements not specifically recited.

Throughout this specification, the user of the phrase 'handheld device', and its variations are to be construed as 'any computing or electronic device that is compact and portable enough to be held and used in one or both hands, such as a smartphone, a tablet computer, or a personal digital assistant.

Figure 1:
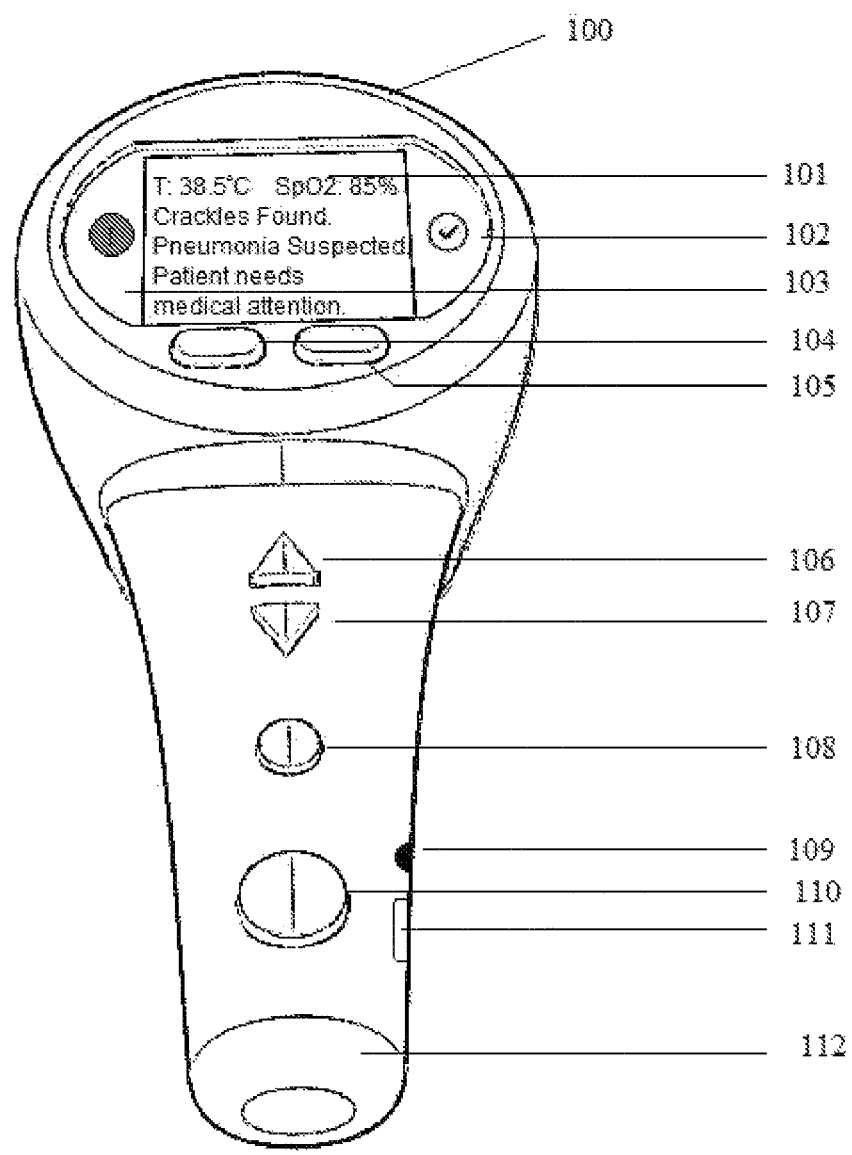
FIG. 1 illustrates an intelligent cardio-pulmonary screening device, in accordance with the present disclosure.
Figure 2:
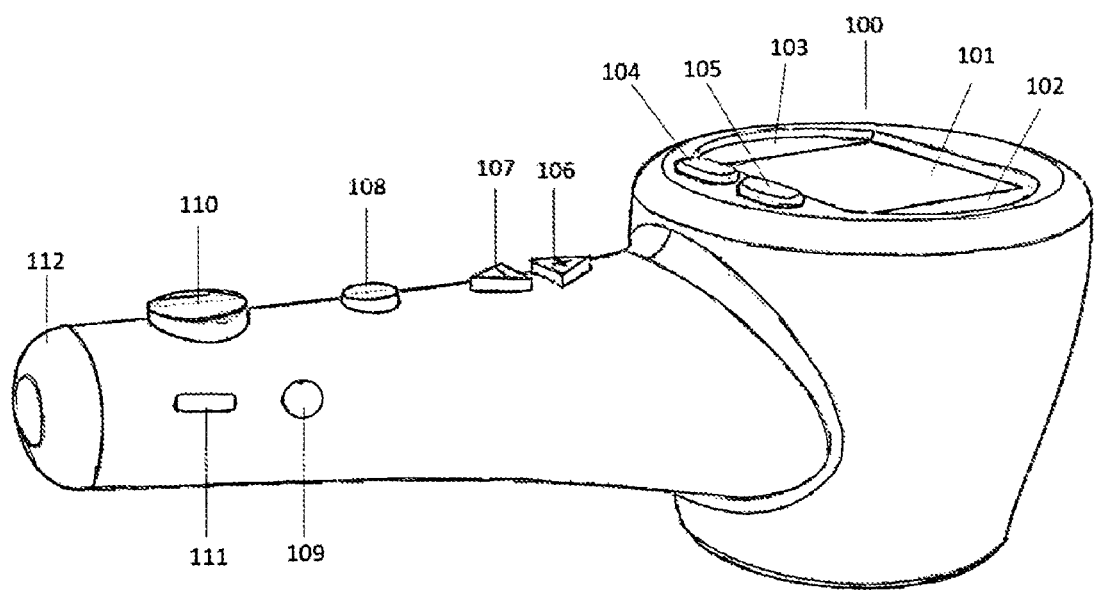
FIG. 2 illustrates a side view of an intelligent cardio-pulmonary screening device, in accordance with the present disclosure.

An intelligent and real-time cardio-pulmonary screening device (100) is disclosed. As shown in FIG. 1 and FIG. 2, the intelligent and real-time cardio-pulmonary screening device (100) comprises a housing that encloses a body.

The body comprises: a display unit (101); a plurality of light emitting diode (LED) indicators (102, 103); a first toggle switch (104); a second toggle switch (105); a plurality of volume controls (106, 107); a third toggle switch (108); an output port (109); a switch (110); a charging port (111); a temperature sensor (not shown) and an oxygen saturation sensor (not shown); and a transducer unit (112).

The plurality of light emitting diode (LED) indicators (102, 103) visually indicates the results of cardio-pulmonary analysis.

The first toggle switch (104) is configured to enable the toggling of the device (100) between a heart monitoring mode and a lung monitoring mode, while the second toggle switch (105) is configured to enable the toggling of the device (100) between an adult mode and a paediatric mode. The third toggle switch (108) is configured to enable the connecting or disconnecting of the device (100) with an application on a handheld device or a wearable device or an application that is installable on a computing device.

The computing device includes, but is not limited to, laptop computers, desktop computers, mobile phones, smart phones, tablets, phablets, and smart watches.

The plurality of volume controls (106, 107) facilitate the increasing or decreasing of the volume of an audio output from the device (100).

The output port (109) facilitates the connecting of an audio playback device; the switch (110) powers the device (100) on or off; the charging port (111) facilities the charging of a rechargeable battery (not shown); the temperature sensor (not shown) facilitates the measuring of the body temperature of a patient; the oxygen saturation sensor facilitates the measuring of the oxygen level of the patient; and the transducer unit (112) is configured to enable the device (100) to receive sound from the chest or the lungs of the patient, said transducer unit (112) being removably attached with the device (100).

The transducer unit (112) receives the chest sound or the sound of the lungs of the patient. Then, the sound is filtered and amplified in real-time. The device (100) has an adaptive noise cancellation system which eliminates ambient noises in the received sound.

Figure 6:
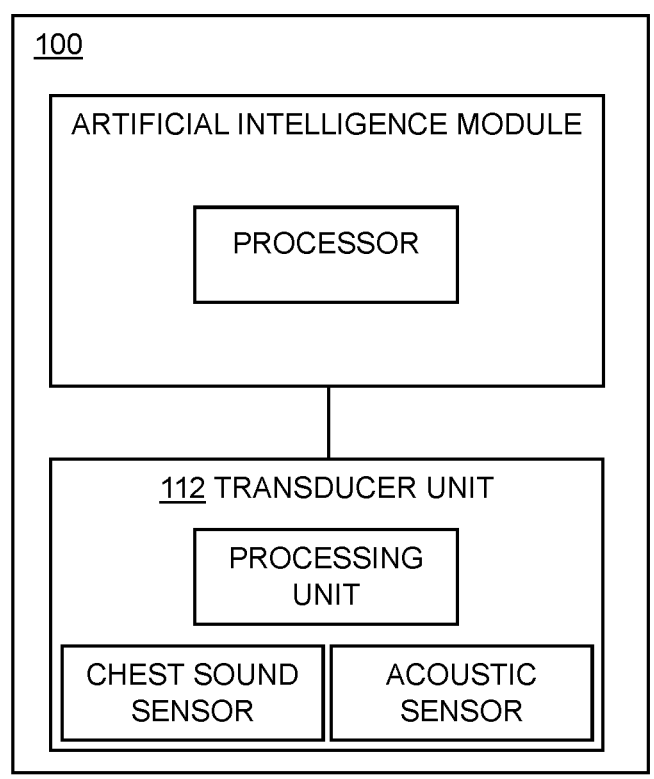
FIG. 6 depicts a block diagram of some internal components of the intelligent cardio-pulmonary screening device, in accordance with the present disclosure.

As shown in FIG. 6, the transducer unit (112) comprises: a microelectromechanical (MEMS) based sensor that picks up chest sound, and an acoustic sensor which picks ambient noise. The ambient noise is removed through filters and adaptive noise cancellation techniques. The sound collected by the chest sensor is amplified and processed through a processing unit.

The second toggle switch (105) allows the device (100) to toggle between an adult mode and paediatric mode during use. Depending on the selected mode, the device (100) filters high frequency sounds or low frequency sounds.

In an embodiment of the present disclosure, the device (100) comprises an in-built artificial intelligence module that analyses the sounds received and presents the results in the display unit (101) as well as in the plurality of the LED indicators (102, 103).

Traditional dual head stethoscope is designed to allow the user to be able to listen to different sound frequencies. The bell, or round side of the drum, is better for hearing low-pitched sounds. Children have thinner chest walls than adults and, therefore, louder breath sounds. Respiratory assessment of a paediatric patient requires age-appropriate alterations. Based on the selected mode, appropriate filters for frequencies are selected. Thus, the device (100) gets optimised for the suitable demography. This also tags the data collected by the device (100) with the type of patient. When the data is synced with the cloud, the previous data gets updated with new data. Similarly, the device (100) syncs the updated data with the on-device local data. This facilitates offline diagnosis with better accuracy. With time, the accuracy and efficiency improve with new data and more classification categories may be added.

The artificial intelligence module comprises an on-board artificial intelligence processor that is configured to run machine learning algorithms on the device (100). This module adds assistive intelligence to the users and ensures that the device (100) can be used by semi-skilled healthcare users and also in remote places, where there is no internet access. Hence there is disadvantage with cloud-based artificial intelligence classification. The on-board artificial intelligence module helps in offline diagnosis. The module syncs from and to the cloud when connected to internet. So, it reduces the dependency on the cloud and internet connectivity.

In another embodiment of the present disclosure, the temperature measured using the temperature sensor is displayed in the display unit (101).

Based on the degree of severity, the device (100) may also send out one or more alerts to a user. The alert may be any type of alert known in the art and includes, but is not limited to, visual alerts, text messages, and sound alerts.

Figure 3:
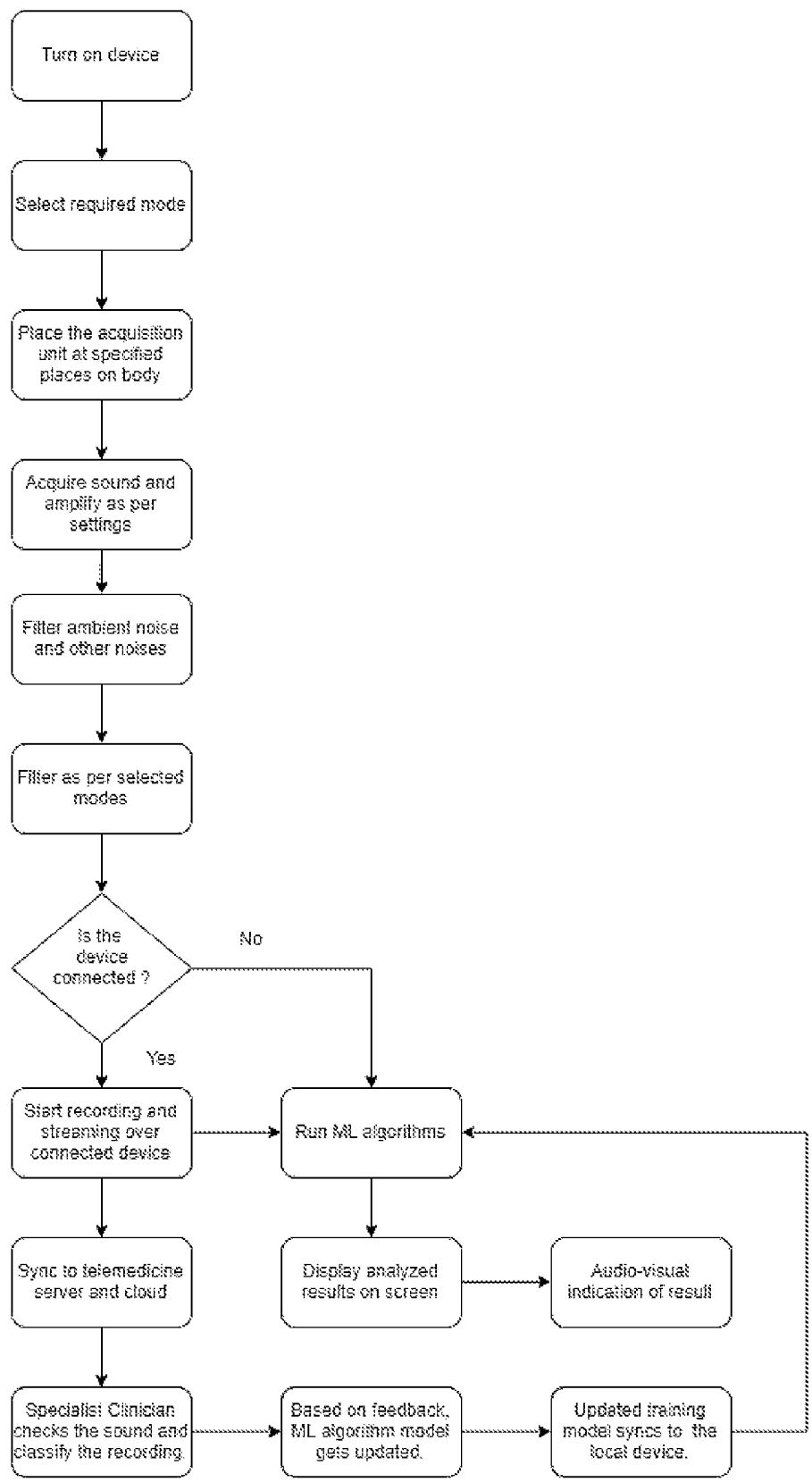
FIG. 3 depicts a flowchart of the functioning of an intelligent cardio-pulmonary screening device, in accordance with the present disclosure.

As shown in FIG. 3, the device (100) receives the chest sound patterns, lung sound patterns, and body temperature in real-time and transmits them to an application on a handheld device, or a wearable device through a communications module. The artificial intelligence module in the device (100) analyses the data in real-time and sends the results to the display unit (101) and to the plurality of LED indicators (102, 103). Further, the data in the application is synced with a server where it may be viewed by one or more healthcare professionals, who provide feedback. The feedback from the one or more healthcare professionals is updated in the artificial intelligence module of the device (100).

The transmission of the data through the communications module may occur through any wired or wireless technology known in the art, including, but not limited to, wireless internet, mobile data, Bluetooth Low Energy, Bluetooth 4.0, Near-Field Communication, LoRa, ZigBee, or the like. The device (100) may be remotely controlled through the application on a handheld device or a wearable device.

In yet another embodiment of the present disclosure, the device (100) may record and store the data in an internal storage and/or external storage. The recorded data can subsequently be streamed over the internet or any other telemedicine channel with a remote pulmonologist or cardiologist (remote clinical observation) for confirmation.

When the device (100) is connected to the application on a handheld device or a wearable device, the application is an interface between the user and expert(s) in remote locations. The application streams the chest sounds with other body parameters, such as temperature, oxygen, and respiratory rate to the expert(s). The application is also configured to allow the user to show the patient through a video channel or interface to the expert(s). The application also allows user to export the plotted data onto a printable format, which can be shared offline for further consultation.

In yet another embodiment of the present disclosure, the data from the application on a handheld device or a wearable device may also be transmitted to the cloud for storage and/or backup purposes.

The handheld device or the wearable device includes, but is not limited to, mobile phones, smart phones, tablets, phablets, and smart watches. The transmission of the real-time data from the device (100) may occur through wireless internet, mobile data, Bluetooth Low Energy, LoRa, ZigBee, or the like.

The device (100) is powered by a rechargeable battery that allows the device (100) to be used for several days without need of charging and can also be charged through a magnetic charger or wireless charger.

Figure 4:
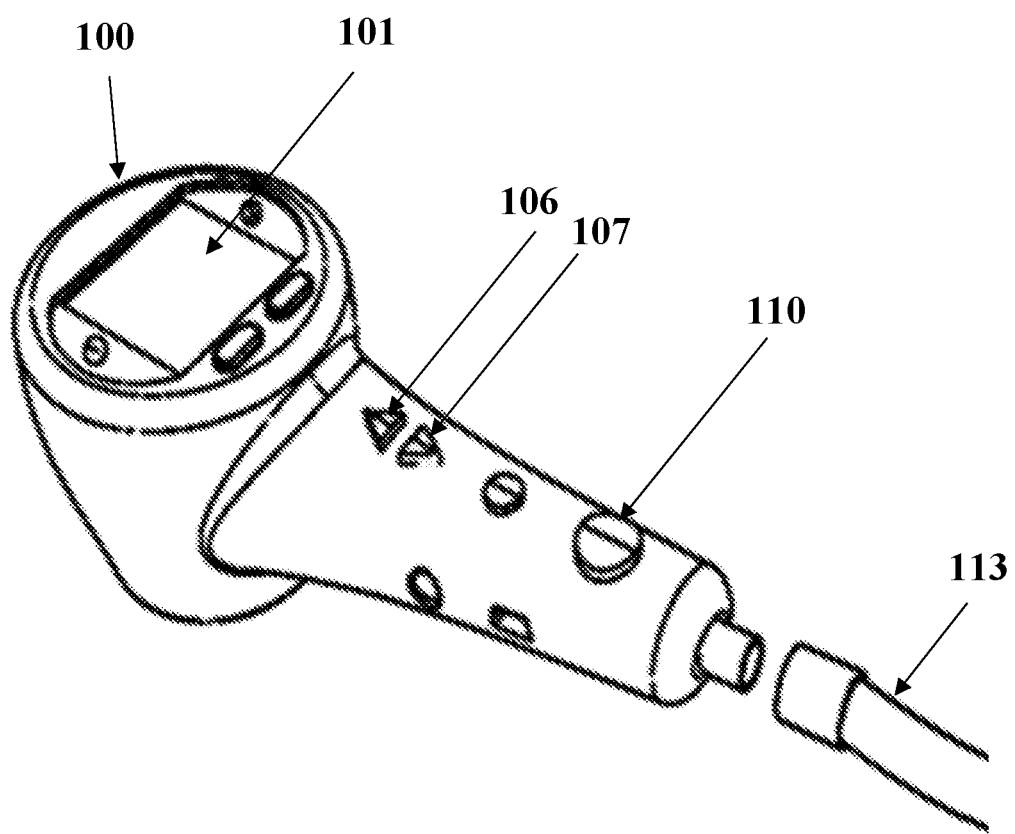
FIG. 4 illustrates an intelligent cardio-pulmonary screening device, in which a binaural with tube is attached to the device, in accordance with the present disclosure.

In yet another embodiment of the present disclosure, as shown in FIG. 4, a binaural with tube (113) is attached to the device (100) to enable a user to use earpieces and a cap is placed when the tube is detached from the device (100).

The disclosed device (100) is an easy to use, affordable, point of care screening device that records sounds from digital auscultation examinations and uses artificial intelligence to classify underlying cardio-pulmonary diseases within a minute. The results of the classification can be confirmed by healthcare experts by sharing the results. The device (100) is suitable to be used by medical as well as paramedical staff. The device (100) can also be used for detecting abnormal foetal heart sounds, Temporomandibular joint (TMJ) sounds, and cardiac murmurs.

Auscultation of the lung is an important part of the respiratory examination and is helpful in diagnosing various respiratory disorders. Auscultation assesses airflow through the trachea-bronchial tree. It is important to distinguish normal respiratory sounds from abnormal ones, for example crackles, rhonchi, wheezes, stridor, and pleural rub, in order to make correct diagnosis. Abnormal breath sounds are usually indicators of problems in the lungs or airways. The most common causes of abnormal breath sounds are pneumonia, heart failure, chronic obstructive pulmonary disease (COPD), such as emphysema, asthma, bronchitis, foreign body in the lungs or airways.

Figure 5:
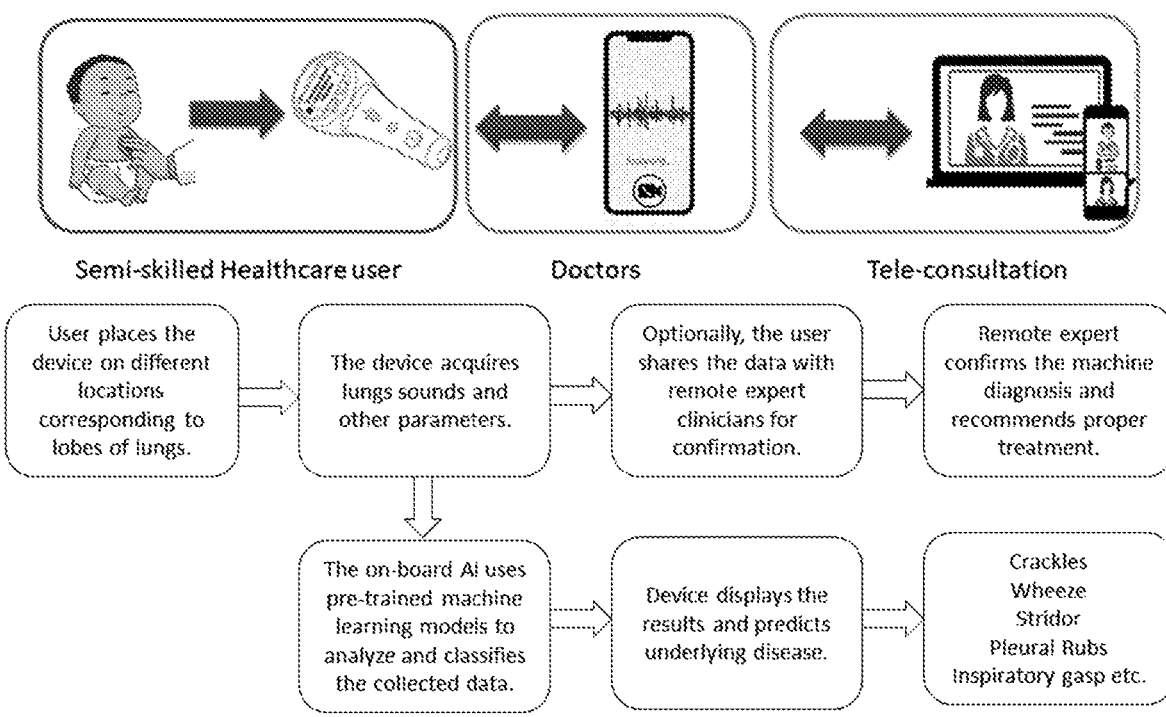
FIG. 5 depicts another flowchart of the functioning of an intelligent cardio-pulmonary screening device, in accordance with the present disclosure.

As shown in FIG. 5, the device (100) analyses and classifies sounds acquired from different chest points during examination. The classification is done by on-board artificial intelligence module. The device (100) gives one or more alerts if the patient needs further medical attention. For example, if there is crackle pattern found in the lungs sound with abnormal temperature and low oxygen, the device may classify the condition as suspected pneumonia and warn user to refer the baby to a pediatrician. This procedure can happen without any internet connectivity.

The display unit (101) displays the classification determined by the device (100). If the user is a semi-skilled user, then the patient is referred to the suitable specialist for further diagnosis, in case of an abnormal pattern (for example, displayed through a red LED). If the user is an advanced user, such as researcher or pulmonologist or pediatrician, then they can use the displayed information to investigate further.

The device (100) can be a hand held one or a wearable one. In wearable form, the device (100) is worn by the patient or wrapped properly as instructed. In wearable form, the device (100) also determines respiratory rate as an additional parameter. The wearable device (100) can be used for long-term, continuous respiratory health monitoring of bed-bound patients.

It will be apparent to a person skilled in the art that the above description is for illustrative purposes only and should not be considered as limiting. Various modifications, additions, alterations and improvements without deviating from the spirit and the scope of the disclosure may be made by a person skilled in the art. Such modifications, additions, alterations and improvements should be construed as being within the scope of this disclosure.

LIST OF REFERENCE NUMERALS

100—An Intelligent Cardio-Pulmonary Screening Device
101—Display Unit
102, 103—Plurality of LED Indicators
104—First Toggle Switch
105—Second Toggle Switch
106, 107—Volume Controls
108—Third Toggle Switch
109—Output Port
110—Switch
111—Charging Port
112—Transducer Unit
113—Binaural with Tube

I claim:

1. An intelligent and real-time cardio-pulmonary screening device, comprising:
    a display unit;
    two light-emitting diode indicators;
    a first toggle switch that is configured to enable a toggling of the device between a heart monitoring mode and a lung monitoring mode, wherein the heart monitoring mode corresponds to analyzing chest sounds, and the lung monitoring mode corresponds to analyzing lung sounds, respectively;
    a second toggle switch that is configured to enable the toggling of the device between an adult mode and a pediatric mode, wherein the adult mode corresponds to analyzing low frequency chest and/or lung sounds, and the pediatric mode corresponds to analyzing high frequency chest and/or lung sounds, respectively;
    two volume controls that facilitate an increasing or decreasing of a volume of an audio output from the device;
    an output port that transmits the audio output from the device, such that the two volume controls facilitate the increasing or decreasing of the volume of the audio output from the device;
    a switch that powers the device on or off;
    a transducer unit that is adapted to filter different frequency ranges of sounds, and is removably attached to the device, said transducer unit including a chest sound sensor which receives the chest or lung sounds and an acoustic sensor that detects ambient noise, and a processing unit which, in real-time, removes the ambient noise from the chest sounds by filtering it using the chosen adult or pediatric mode performs adaptive noise cancellation techniques and then amplifies the sound; and
    a processor configured to analyze the chest sounds and the lung sounds received in real-time from the chest sound sensor of the transducer unit and present the results in the display unit, as well as via the two light-emitting diode indicators, and further configured to visually indicate the results of cardio-pulmonary analysis by way of the two light-emitting diode indicators, wherein the processor auto-analyses and classifies a condition of the patient by way of the cardio pulmonary analysis, involving chest sound patterns, lung sound patterns, body temperature and oxygen level data of the patient.

2. The intelligent and real-time cardio-pulmonary screening device as claimed in claim 1, wherein the device sends out one or more alerts to the user.

3. The intelligent and real-time cardio-pulmonary screening device as claimed in claim 1, wherein the device also determines respiratory rate as an additional parameter.

* * * * *